(12) United States Patent
Gardon-Mollard

(10) Patent No.: US 6,247,185 B1
(45) Date of Patent: Jun. 19, 2001

(54) COMPRESSIVE SUPPORT ORTHOSIS TIGHTS, PARTICULARLY FOR THE POSTPARTUM PERIOD

(75) Inventor: Christian Gardon-Mollard, Chamalieres (FR)

(73) Assignee: Innothera Topic International société anonyme, Arcueil (FR)

( * ) Notice: Subject to any disclaimer, the term of this patent is extended or adjusted under 35 U.S.C. 154(b) by 0 days.

(21) Appl. No.: 09/194,407
(22) PCT Filed: May 29, 1997
(86) PCT No.: PCT/FR97/00933
  § 371 Date: Jan. 7, 1999
  § 102(e) Date: Jan. 7, 1999
(87) PCT Pub. No.: WO97/45080
  PCT Pub. Date: Dec. 4, 1997

(30) Foreign Application Priority Data

May 30, 1996 (FR) .................................. 96 06672

(51) Int. Cl.$^7$ ........................................ A41B 9/00
(52) U.S. Cl. ................................... 2/409; 2/239
(58) Field of Search .................. 2/409, 239, 78.1–78.4, 2/227, 406, 69, 243.1; 450/155; 66/177, 178 R, 171, 172 R, 173, 175, 176, 194, 195, 169 R, 197, 170, 198, 172, 199, 179, 180–189, 178 A, 191–193, 200, 202, 169

(56) References Cited

U.S. PATENT DOCUMENTS

| 3,595,034 | * | 7/1971 | Safrit | 2/409 |
| 4,106,514 | | 8/1978 | Lowth . | |

FOREIGN PATENT DOCUMENTS

| 953939 | * | 9/1974 | (CA) | 2/409 |
| 2530783 | * | 6/1955 | (DE) | 2/409 |
| 7515833 | | 8/1976 | (DE) . | |
| 732192 | * | 6/1955 | (IT) | 2/409 |

* cited by examiner

Primary Examiner—Gloria M. Hale
(74) Attorney, Agent, or Firm—Jacobson Holman PLLC

(57) ABSTRACT

A compressive elastic-tights orthosis with an abdominal portion, or compressive knit, having a waist, front, back and, and groin, and adjoining two leg portions of compressive knit, the abdominal portion having a substantially triangular starched front region extending inward from the waist to the groin and having little deformability by providing high-pressure elasticity in both lateral and vertical directions, whereby, when the orthosis is worn, the front region exerts substantially constant pressure against the abdomen, in opposition to deformation of the abdomen, and the two leg portions exert vascular pressure on the lower limbs.

4 Claims, 1 Drawing Sheet

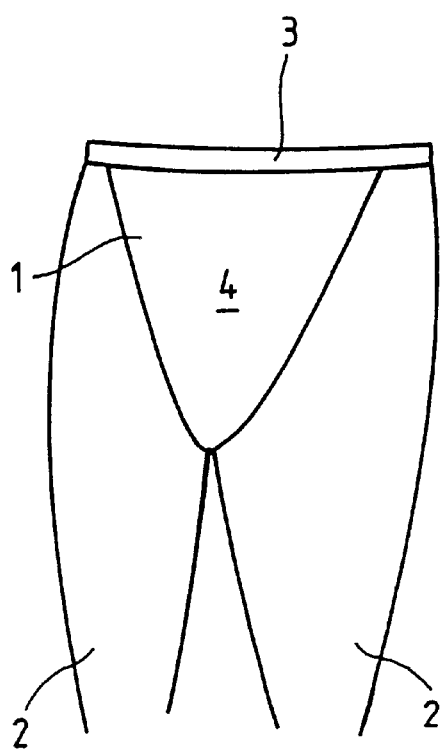
FIG_1
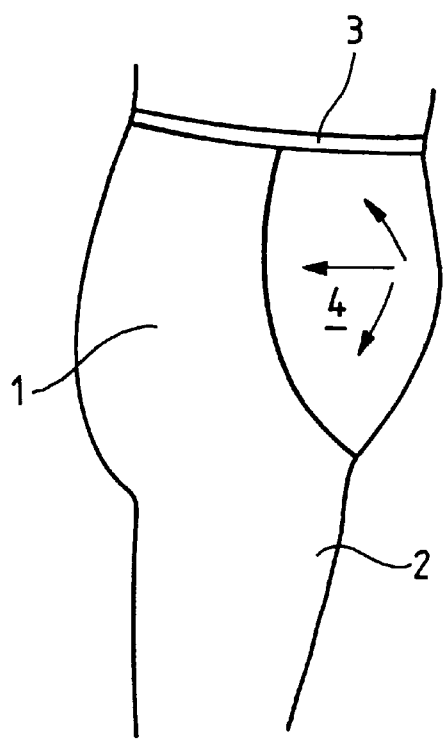
FIG_2

COMPRESSIVE SUPPORT ORTHOSIS TIGHTS, PARTICULARLY FOR THE POST-PARTUM PERIOD

The invention relates to the field of compressive orthoses for the lower limbs, and generally known as "elastic tights".

Such elastic tights serve to apply strong compression to the lower limbs with pressure that decreases progressively from the ankle, and they are indicated for various syndromes involving venous insufficiency. They are made of elastic material, typically a knit of very fine mesh, with the tights being very accurately dimensioned so as to provide the looked-for degressive pressure.

Insofar as it is desired to apply compression to the lower limbs that decreases on going up the leg, the abdominal portion is a portion of relatively low elasticity, and does not provide significant compression (compressive support) of the abdomen.

It is often desired, in particular for pregnancy tights (as in DE-U-751 5833), to reduce elasticity in the abdomen zone in order to make this portion of the tights more deformable, thereby enabling the tights to adapt appropriately to the changes in volume of the abdomen during pregnancy.

In contrast, the object of the invention is to provide elastic tights that provide significant compression of the abdomen (i.e. tights that are not very deformable in this region), in combination with compression of the lower limbs, and suitable for use in particular in rehabilitation of the abdomen after giving birth (postpartum).

More precisely, the compressive orthosis of the invention, which includes an abdominal portion of compressive knit and two attached leg portions, also of compressive knit, is characterized in that the abdominal portion includes, in the front, a region of increased elasticity and of substantially triangular shape extending between the waist and the groin, said region of reinforced elasticity being suitable and intended, particularly during the post-partum period, for exerting substantially constant pressure on the abdomen in combination with vascular pressure on the lower limbs by means of the leg portions.

In a first implementation, the region of increased elasticity is formed by adding a patch of cloth having reinforced two-dimensional elasticity. In another implementation, it is formed by knitting elastic reinforcement.

Such a structure makes it possible to exert constant pressure on the abdomen and to provide the patient with continuous help and comfort during the period of rehabilitation that follows childbirth.

An embodiment of the invention is described below with reference to the accompanying drawing.

FIG. 1 is a front view of elastic tights of the invention.

FIG. 2 is a side view of the same tights.

In the figures, there is shown in diagrammatic manner a compressive orthosis in the form of a pair of elastic tights having an abdominal portion 1 of compressive knit and two associated leg portions 2, likewise of compressive knit.

The knit is conventional, the invention being applicable to any knit structure known to a specialist in knitting techniques (weft knit, plain knit, ribbed, nipped-in or float stitch micromesh, etc.).

This type of knit is used, for example, in the elastic stockings and tights sold by Innothera Topic under the registered trademark Varisma.

The materials used may be elastane covered in cotton and polyamide, elastane covered in polyamide but without cotton, or indeed a mixture of elastane and elasto-diene (rubber latex).

To enable significant pressure to be applied to the abdomen, a highly elastic patch 4 is provided in a substantially triangular region defined by the waist 3 and by the groin, said patch being made, for example, of compressive elastic cloth of the type given reference No. 13638-6 by the firm Elastic (of Catteins, Austria).

The patch can be a knit, a warp and weft structure, a woven weave, etc.

In a variant, this highly elastic portion 4 can be made by knitting (knitting elastic reinforcement).

The main characteristic of the portion 4, whether it is an add-on patch or part of the knitting, is that it provides high-pressure elasticity in both directions, so that it acts like a starched front.

The knitting of the portion 4 can be implemented using any known type of knit, with or without a thread that is plated (i.e. with an additional thread being included while knitting is being performed).

The article made in this way provides combined compression of the abdomen and of the lower limbs, which combined compression is particularly indicated for syndromes of venous insufficiency induced by pregnancy, or associated with the period preceding and following childbirth.

During the period of abdominal rehabilitation after childbirth, the effect of compressing the abdomen is to push back the waist of the abdomen as extended by pregnancy, in opposition to the natural deformation of the abdomen.

What is claimed is:

1. A compressive elastic-tights orthosis, comprising: (a) an abdominal portion, of compressive knit, having a waist, front, back and, and groin, and adjoining (b) two leg portions of compressive knit, characterized in that said abdominal portion including a substantially triangular starched front region extending inward from the waist to the groin and having little deformability by providing high-pressure elasticity in both lateral and vertical directions, whereby, when said orthosis is worn, said front region exerts substantially constant pressure against the abdomen, in opposition to deformation of the abdomen, and said two leg portions exert vascular pressure on the lower limbs.

2. A compressive orthosis of elastic tights type, comprising an abdominal portion (1) of compressive knit and two adjoining leg portions (2), likewise of compressive knit, said abdominal portion including, in front, a region (4) of substantially triangular shape extending between waist and groin, characterized in that said region (4) extending between the waist and the groin is a region with little deformability forming a starched front, providing high-pressure elasticity in both dimensions, whereby said region exerts on the abdomen during the post-partum period a substantially constant pressure in opposition to the deformation of the abdomen, in combination with vascular pressure on the lower limbs by means of the leg portions.

3. A compressive orthosis of claim 2, wherein said front region is formed by a cloth patch having two-dimensional elastic reinforcement.

4. The compressive orthosis of claim 3, wherein said front region is formed by knitting elastic reinforcement into the abdominal portion.

* * * * *